United States Patent [19]

Hager et al.

[11] Patent Number: 5,424,385
[45] Date of Patent: Jun. 13, 1995

[54] PHOSPHAZENES CONTAINING ORGANOSILICON RADICALS, PROCESS FOR THEIR PREPARATION AND THEIR USE

[75] Inventors: Rudolf Hager, Altoetting; Bernward Deubzer; Otto Schneider, both of Burghausen, all of Germany

[73] Assignee: Wacker-Chemie GmbH, Munich, Germany

[21] Appl. No.: 248,778

[22] Filed: May 25, 1994

[30] Foreign Application Priority Data

May 28, 1993 [DE] Germany .................... 43 17 978.9

[51] Int. Cl.$^6$ .................... C08G 77/26; C08G 77/30
[52] U.S. Cl. ..................... 528/28; 556/405; 556/413; 528/25; 528/23; 528/399
[58] Field of Search .............. 556/405, 413; 528/28, 528/25, 23, 399

[56] References Cited

U.S. PATENT DOCUMENTS

| | | | |
|---|---|---|---|
| 3,839,388 | 10/1974 | Nitzsche et al. | 556/450 |
| 4,218,556 | 8/1980 | Hergenrother et al. | 528/168 |
| 4,377,558 | 3/1983 | De Jaeger et al. | 423/300 |
| 4,544,536 | 10/1985 | De Jaeger et al. | 423/300 |
| 4,710,549 | 12/1987 | Pettigrew | 525/538 |
| 4,720,533 | 1/1988 | Pettigrew | 528/28 |
| 4,784,918 | 11/1988 | Klett et al. | 428/447 |
| 4,835,237 | 5/1989 | Burkhardt et al. | 528/21 |

FOREIGN PATENT DOCUMENTS

| | | |
|---|---|---|
| 0026685 | 4/1981 | European Pat. Off. |
| 0305737 | 3/1989 | European Pat. Off. |
| 0394918 | 10/1990 | European Pat. Off. |
| 2229514 | 1/1979 | Germany . |
| 3725377 | 2/1989 | Germany . |
| 2252975 | 8/1992 | United Kingdom . |
| 446525 | 10/1974 | U.S.S.R. . |

OTHER PUBLICATIONS

AN 89–047561/07 the English Derwent Abstract.
M. Bermann et al. "The Phosphazotrihalides", Advances in Inorganic and Radiochemistry 14 (1972), Academic Press New York, London, pp. 1–30.

Primary Examiner—John C. Bleutge
Assistant Examiner—Margaret W. Glass
Attorney, Agent, or Firm—Martin Connaughton

[57] ABSTRACT

The present invention relates to oxygen-containing chlorophosphazenes containing organosilicon radicals, in particular those of the formula $$Z-PCl_2=N(-PCl_2=N)_n-PCl_2O \qquad (I)$$

in which

Z is an organosilicon radical bonded to phosphorus via oxygen and n is from 0 to 6, processes for their preparation and their use in processes for the condensation and/or equilibration of organosilicon compounds.

5 Claims, No Drawings

PHOSPHAZENES CONTAINING ORGANOSILICON RADICALS, PROCESS FOR THEIR PREPARATION AND THEIR USE

FIELD OF INVENTION

The present invention relates to a process for the preparation and use for oxygen-containing chlorophosphazenes having organosilicon radicals bonded to phosphorus via oxygen by condensation and/or equilibration of organosilicon compounds.

BACKGROUND OF INVENTION

Chlorophosphazenes, which are often called phosphonitrile chlorides or phosphorus nitride chlorides, are already known as catalysts for condensation and/or equilibration reactions of organosilicon compounds. Reference may be made to DE 22 29 514 B (Wacker-Chemie GmbH, published on Apr. 20, 1978) and the corresponding U.S. Pat. No. 3,839,388, (issued Oct. 1, 1974) in which chlorophosphazenes with a ratio of phosphorus to nitrogen of greater than one are described. The limited solubility of these catalysts, consisting essentially of ionic phosphazene units, in organic solvents is a disadvantage. DE 37 25 377 A (Wacker-Chemie GmbH; published on Feb. 9, 1989) describes the reaction of these phosphonitrile chlorides with cyclic diorganopolysiloxanes. In contrast, oxygen-containing chlorophosphazenes, in particular phosphoryl chlorophosphazenes, or chlorophosphazenes having at least one $PCl_2O$ group, which are likewise suitable catalysts for condensation and/or equilibration reactions of organosilicon compounds, are soluble in most organic solvents. However, organic solvents are generally undesirable. In such cases, the oxygen-containing chlorophosphazenes, many of which are liquid, can also be employed without a solvent, but this often leads to problems, particularly in metering or homogeneous distribution of the catalyst in the reaction mixture.

SUMMARY OF INVENTION

The present invention relates to oxygen-containing chlorophosphazenes containing organosilicon radicals.

The oxygen-containing chlorophosphazenes containing organosilicon radicals are preferably those of the formula $$Z-PCl_2=N(-PCl_2=N)_n-PCl_2O \qquad (I),$$

in which

Z represents an organosilicon radical bonded to phosphorus via oxygen and n represents 0 or an integer from 1 to 6, preferably 0 or an integer from 1 to 4, more preferably an integer from 1 to 3.

Although not expressed by formula (I), all or some of the chlorine atoms can be replaced by radicals Q, in which Q represents, monovalent organic radicals, such as alkoxy radicals, aryloxy radicals, halogen atoms other than chlorine, organosilicon radicals and phosphorus-containing radicals.

The oxygen-containing chlorophosphazenes of formula (I) containing organosilicon radicals are preferably those in which the chlorine atom is not substituted by a radical Q.

The following tautomerism exists in the oxygen-containing chlorophosphazenes according to the invention containing organosilicon radicals: 

All statements on compounds having SiOP bonds, apply without restriction to the corresponding tautomers.

The organosilicon radicals Z are preferably radicals, bonded to phosphorus via oxygen, consisting essentially of units of the formula

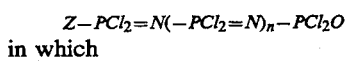 (II)

in which

R may be identical or different and represents a hydrogen atom or a monovalent organic radical, X may be identical or different and represents a chlorine atom or a radical $-OR^1$, where $R^1$ is a monovalent organic radical, a is 0, 1, 2 or 3, preferably 1, 2 or 3, more preferably 2 or 3, and b is 0, 1, 2, preferably 0 or 1, with the proviso that the sum of a+b is less than or equal to 3.

The average value of a is preferably between 1.5 and 3, more preferably between 1.8 and 2.7.

The average value of b is preferably between 0 and 1, more preferably between 0.01 and 0.5.

The radicals R are preferably optionally substituted hydrocarbon radicals having 1 to 12 carbon atoms, hydrocarbon radicals having 1 to 6 carbon atoms, the methyl radical, being more preferred.

Examples of radicals R are alkyl radicals, such as the methyl, ethyl, n-propyl, isopropyl, n-butyl, isobutyl, tert-butyl, n-pentyl, isopentyl, neopentyl and tert-pentyl radical, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, decyl radicals, such as the n-decyl radical, and dodecyl radicals, such as the n-dodecyl radical; alkenyl radicals, such as the vinyl, allyl, 3-norbornenyl, n-5-hexenyl and 4-vinylcyclohexyl radical; cyclo-alkyl radicals, such as cyclopentyl, cyclohexyl, 4-ethylcyclohexyl and cycloheptyl radicals, norbornyl radicals and methylcyclohexyl radicals; aryl radicals, such as the phenyl, naphthyl and biphenylyl radical; alkaryl radicals, such as o-, m- and p-tolyl radicals, xylyl radicals and ethylphenyl radicals; and aralkyl radicals, such as the benzyl radical and the α- and the β-phenylethyl radical.

Examples of monovalent, substituted hydrocarbon radicals R are cyanoalkyl radicals, such as the β-cyanoethyl radical, halogenoalkyl radicals, such as the 3,3,3-trifluoropropyl radical and the V-chloropropyl radical, halogenoaryl radicals, such as o-, m- and p-chlorophenyl radicals, and acyloxyalkyl radicals, such as the V-acryloxypropyl radical and the V-methacryloxypropyl radical.

The radicals $R^1$ are preferably alkyl radicals having 1 to 4 carbon atoms, more preferably the methyl and the ethyl radical.

Examples of X as the radical $-OR^1$ are alkoxy radicals, such as the methoxy and the ethoxy radical.

The oxygen-containing chlorophosphazenes containing organosilicon radicals are preferably those having a molecular weight of 300 to 30000.

Examples of the phosphazenes containing organosilicon radicals are $Me_3SiO-PCl_2=N-PCl_2O$, $Me_2ViSi$-

O—PCl₂=N—PCl₂O,
₅O—PCl₂=N—PCl₂O,
₁₀O—PCl₂=N—PCl₂=N—PCl₂O,
₄₀O—PCl₂=N—PCl₂=N—PCl₂O, Me₂ClSi[OSiMe₂]-
₄O—PCl₂=N—PCl₂=N—PCl₂O, Me₂ClSi[OSiMe₂]₁₀₀₀O—PCl₂=N—PCl₂=N—PCl₂O, Me₂(MeO)-Si[OSiMe₂]₅₀O—PCl₂=N—PCl₂=N—PCl₂O, Me(EtO)₂SiO—PCl₂=N—PCl₂=N—PCl₂O, Me₃SiO—PCl₂=N(—PCl₂=N)₂—PCl₂O, Me₂PhSiO—PCl₂=N(—PCl₂=N)₂—PCl₂O, Me₂ClSi[OSiMe₂]₈O—PCl₂=N(—PCl₂=N)₂—PCl₂O, Me₂ClSi[OSiMe₂]₄O—PCl₂=N(—PCl₂=N)₃—PCl₂O, (Me₃SiO)₂MeSiO—PCl₂=N(—PCl₂=N)₃—PCl₂O, Me₂ClSi[OSiMe₂]₄O—PCl₂=N(—PCl₂=N)₄—PCl₂O, and Me₃Si[OSiMe₂]₁₀O—PCl₂=N(—PCl₂=N)₅—PCl₂O, wherein Me is the methyl radical,
Ph is the phenyl radical and
Vi is the vinyl radical.

The present invention further relates to a process for the preparation of oxygen-containing chlorophosphazenes containing organosilicon radicals, which comprises reacting at least one oxygen-containing chlorophosphazene of the formula $$PCl_3=N(-PCl_2=N)_n-PCl_2O \qquad (III),$$

in which n represents 0 or an integer from 1 to 6, preferably 0 or an integer from 1 to 4, more preferably an integer from 1 to 3, with at least one organosilicon compound consisting essentially of units of the formula $$R_c^2(R^3O)_d SiO_{\frac{4-d-c}{2}} \qquad (IV)$$

in which

R² may be identical or different and is the same as the radical R above,
R³ may be identical or different and is the same as the radical R¹ above,
c is 0, 1, 2 or 3, preferably 1, 2 or 3, more preferably 2 or 3, and
is 0, 1, 2 or 3, preferably 0, 1 or 2, more preferably 0 or 1, with the proviso that the sum of c+d is less than or equal to 4.

All or some of the chlorine atoms in formula (III) may be replaced by radicals Q, in which Q is the same as above.

The oxygen-containing chlorophosphazenes of formula (III) are preferably those in which no chlorine atom is substituted by a radical Q.

The average value of c is preferably between 1.5 and 3, more preferably between 1.8 and 2.7.

The average value of d is preferably between 0 and 1, more preferably between 0 and 0.5.

Examples of compounds of formula (III) are
PCl₃=N—PCl₂O,   PCl₃=N—PCl₂=N—PCl₂O,
PCl₃=N(—PCl₂=N)₂—PCl₂O,
PCl₃=N(—PCl₂=N)₃—PCl₂O,
PCl₃=N(—PCl₂=N)₄—PCl₂O,
PCl₃=N(—PCl₂=N)₅—PCl₂O,
PCl₃=N(—PCl₂=N)₆—PCl₂O,
PCl₃=N—PCl(N=PCl₃)—PCl₂O and
PCl₃=N—P(N=PCl₃)₂—PCl₂O, where
PCl₃=N—PCl₂,   PCl₃=N—PCl₂=N—PCl₂O,
PCl₃=N(—PCl₂=N)₂—PCl₂O,
PCl₃=N(—PCl₂=N)₃—PCl₂O,
PCl₃=N(—PCl₂=N)₄—PCl₂O, and
PCl₃=N(—PCl₂=N)₅—PCl₂O are preferred and
PCl₃=N—PCl₂=N—PCl₂O,
PCl₃=N(—PCl₂=N)₂—PCl₂O and
PCl₃=N(—PCl₂=N)₃—PCl₂O are more preferred.

Examples of organosilicon compounds of formula (IV) employed in the process are silanes, such as Me₃SiOMe, Me₃SiOEt, Me₂Si(OMe)₂, Me₂Si(OEt)₂, MeSi(OMe)₃, Me₂ViSiOMe, Me₂OctSiOMe and Me₂EtSiOMe, as well as organopolysiloxanes, such as Me₃SiOSiMe₃, [Me₂SiO]₃, [Me₂SiO]₄, [Me₂SiO]₅, [Me₂SiO]₆, Me₃Si[OSiMe₂]₁₀OSiMe₃, Me₃Si[OSiMe₂]₁₀₀OSiMe₃, Me₃Si[OSiMe₂]₁₅₀OSiMe₃, Me₂(MeO)Si[OSiMe₂]₅₀OSiMe₂(OMe), Me₃SiOSiMe(OMe)OSiMe₃, Me₂ViSi[OSiMe₂]₅₀OSiMe₂Vi, (EtO)₂MeSi[OSiMe₂]₁₀₀OSiMe(OEt)₂, Me₃Si[OSiMe₂]₅₀OSiMe(CH₂CH₂CF₃)]₈OSiMe₃, Me₃Si[OSiMe₂]₈₀OSiMeH]₅OSiMe₃ and Me₃Si[OSiMe₂]₂₀[OSiPhMe]₂₀OSiMe₃, where Me₃SiOSiMe₃, [Me₂SiO]₃, [Me₂SiO]₄, [Me₂SiO]₅, Me₃Si[OSiMe₂]₁₀OSiMe₃, Me₃Si[OSiMe₂]₁₀₀OSiMe₃, Me₃Si[OSiMe₂]₈₀[OSiMeH]₅OSiMe₃ and Me₂(MeO)Si[OSiMe₂₅₀OSiMe₂(OMe) are preferred and [Me₂SiO]₄, Me₃Si[OSiMe₂]₁₀OSiMe₃ and Me₃Si[OSiMe₂]₁₀₀OSiMe₃ are particularly preferred and Me represents the methyl radical,
Et represents the ethyl radical,
Oct represents the n-octyl radical,
Ph represents the phenyl radical and
Vi represents the vinyl radical.

The term organopolysiloxanes is also understood as meaning oligomeric siloxanes.

If the organosilicon compounds consisting essentially of units of formula (IV) are organopolysiloxanes, a viscosity of 0.6 to 1000 mm²/s is preferred.

The organosilicon compound consisting essentially of units of formula (IV) is preferably employed in the process in amounts of 20% to 10000% by weight, more preferably 50% to 5000% by weight, based on the total weight of oxygen-containing chlorophosphazenes of formula (III).

The process is preferably carried out at a temperature of 20° C. to 170° C., more preferably 30° C. to 130° C., under a pressure of 50 to 1100 hPa, more preferably 900 to 1100 hPa.

The process can be carried out in the presence or absence of an organic solvent, preferably no organic solvent being employed.

If the organosilicon compound employed is an organopolysiloxane consisting essentially of units of formula (IV) where d is 0, temperatures of about 100° C. are often necessary in order to obtain an appropriate rate of reaction. It has been proven advantageous to add organic solvent, especially when longer-chain chlorophosphazenes of formula (III) where n≧3, are additionally employed.

If organic solvents are employed in the process, they are preferably those which are inert towards the oxygen-containing chlorophosphazenes of formula (III) containing organosilicon compounds of formula (IV) and the phosphazenes containing organosilicon radicals, and which have boiling points under a pressure of 1 hPa of not more than 120° C., which means they can be removed again in a relatively simple manner by distillation.

Examples of such organic solvents are chlorohydrocarbons, such as chloroform, isomeric trichloroethanes, trichloroethene, isomeric tetrachloroethanes, tetrachloroethene and 1,2,3-trichloropropane; ethers, such as dioxane, tetrahydrofuran, diethyl ether and diethyleneglycol dimethyl ether; esters, such as methyl acetate, ethyl acetate, n- and iso-propyl acetate, diethyl carbonate and ethyl formate; and hydrocarbons, such as n-hexane, a hexane isomer mixture, cyclohexane, heptane, octane, wash benzine, petroleum ether, benzene, toluene and xylenes, where hydrocarbons, in particular toluene and xylenes, and chlorohydrocarbons, in particular chloroform, tri- and tetrachloroethene and 1,2,3-trichloropropane, are more preferred.

If solvent is co-used, an amount of 20% to 500% by weight, in particular 50% to 300% by weight, based on the total amount of chlorophosphazene of formula (III) and organosilicon compound consisting essentially of units of formula (IV), is preferably employed.

The individual constituents employed in the process can be one type of such constituents or a mixture of such constituents.

The process is preferably carried out with exclusion of substances containing hydroxyl groups, such as water, alcohols, carboxylic acids and siloxanols.

In a preferred embodiment of the process, the oxygen-containing chlorophosphazene of formula (III) and organosilicon compound consisting essentially of units of formula (IV) are mixed thoroughly and stirred intensively. As soon as the reaction mixture is homogeneous, stirring is continued for an additional hour. If the reaction is carried out in the presence of an organic solvent, the reaction has ended when the reaction mixture remains homogeneous after removal of the organic solvent.

The oxygen-containing chlorophosphazenes containing organosilicon radicals are liquid, oily or pasty substances, the consistency being influenced either more by the nature of the chlorophosphazene or by the nature of the organosilicon radical, depending on which content predominates in the molecule.

The process has the advantage that oxygen-containing chlorophosphazenes containing organosilicon radicals can be prepared in a simple manner.

The process also has the advantage that bonding of the organosilicon radicals to the phosphazenes proceeds with an exceptionally high selectivity.

Although the chlorophosphazenes of formula (III) contain several phosphorus-chlorine groups, an SiOP bond is linked only on the terminal phosphorus atom which does not contain oxygen.

The organosilicon compounds consisting essentially of formula (IV) are commercially available compounds or can be prepared by the methods customary in silicon chemistry.

The oxygen-containing chlorophosphazenes of formula (III) may be synthesized by known processes. Reference may be made to M. Bermann: "The Phosphazatrihalides", Advances in Inorganic and Radiochemistry 14 (1972), Academic Press New York, London, pages 1 to 30. Oxygen-containing chlorophosphazenes can also be prepared by reaction of ionic chlorophosphazenes with compounds containing hydroxyl groups.

The invention further relates to a process for the preparation of oxygen-containing chlorophosphazenes, which consists essentially of reacting ionic chlorophosphazenes of formula

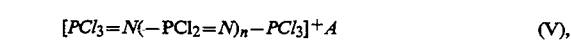

$$[PCl_3=N(-PCl_2=N)_n-PCl_3]^+A \qquad (V),$$

in which n represents 0 or an integer from 1 to 6, preferably 0 or an integer from 1 to 4, more preferably an integer from 1 to 3, and A is a singly negatively charged ion, with compounds containing hydroxyl groups.

The oxygen-containing chlorophosphazenes obtained by this process have the formula

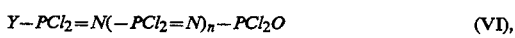

$$Y-PCl_2=N(-PCl_2=N)_n-PCl_2O \qquad (VI),$$

in which n is the same as above and Y represents a chlorine radical or hydroxyl group.

Although not expressed by the formulae (V) and (VI), all or some of the chlorine atoms can be replaced by radicals Q, in which Q is the same as above.

The compounds of formulae (V) and (VI) are preferably those in which the chlorine atom is not substituted by a radical Q.

If Y is a hydroxyl group, the following tautomerism exists:

$$HO-PCl_2=N(-PCl_2=N)_n-PCl_2O \longleftrightarrow O=PCl_2-NH(-PCl_2=N)_n-PCl_2O$$

(VI)            (VI')

where n is the same as above, the equilibrium being more on the left-hand side at compound (VI), at pH<7 and more on the right-hand side at compound (VI'), at pH>7.

If Y is a hydroxyl group and the phosphazenes have more than three phosphorus atoms, there are other canonical structures concerning the central chain members, such as,

$$HO-PCl_2=N(-PCl_2=N)_n-PCl_2O \longleftrightarrow O=PCl_2-NH(-PCl_2=N)_n-PCl_2O$$

(VI)            (VI')

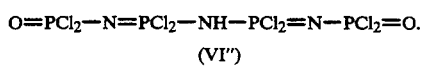

$$O=PCl_2-N=PCl_2-NH-PCl_2=N-PCl_2=O.$$

(VI")

All the following statements on compounds of formula (VI) where Y is OH are intended to apply without restriction to tautomeric compounds, such as those of formulae (VI') and (VI").

A preferably represents a halide ion, in particular chloride, or an adduct of a halide ion with a Lewis acid of the formula $[M_mD_{m+1}]^-$, in which m represents the valency or oxidation state of the central element M and D represents a halogen atom.

A preferably has the formula $[M_mD_{m+1}]^-$ of $BF_4^-$, $BCl_4^-$, $AlCl_4^-$, $FeCl_4^-$, $PF_6^-$, $PCl_6^-$, $SbF_6^-$, $SbCl_6^-$, $HgI_3^-$, $NbCl_6^-$, $MoCl_6^-$, $TaCl_6^-$, where the hexachlorophosphate ion is more preferred.

Examples of the ionic phosphazenes of formula (V) employed in the process are $[PCl_3=N-PCl_3]^+Cl^-$, $[PCl_3=N-PCl_3]^+AlCl_4^-$, $[PCl_3=N-PCl_3]^+BCl_4^-$,

[PCl3=N—PCl3]+FeCl4−,
[PCl3=N—PCl3=N—PCl3]+PCl6−,
[PCl3=N—PCl3]+SbCl6−,   [PCl3=N—PCl3]+Br−,
[PCl3=N—PCl2=N—PCl3]+Cl−,
[PCl3=N—PCl2=N—PCl3]+TaCl6−,
[PCl3=N—PCl2=N—PCl3]+$BCl_4^-$,
[PCl3=N—PCl2=N—PCl3]+FeCl4−,
[PCl3=N—PCl2=N—PCl3]+PCl6−,
[PCl3=N—PCl2=N—PCl3]+SbCl6−,
[PCl3=N—PCl2=N—PCl3]+BR−,
[PCl3=N(—PCl2=N)2—PCl3]+Cl−,
[PCl3=N(—PCl2=N)2 —PCl3]+$AlCl_4^-$,
[PCl3=N(—PCl2=N)2—PCl3]+BCl4−,
[PCl3=N(—PCl2=N)2—PCl3]+MoCl6−,
[PCl3=N(—PCl2=N)2—PCl3]+PCl6−,
[PCl3=N(—PCl2=N)2—PCl3+SbCl6−,
[PCl3=N(—PCl2=N)2—PCl3]+Br−,
[PCl3=N(—PCl2=N)3—PCl3]+Cl−,
[PCl3=N(—PCl2=N)3—PCl3]+PCl6−,
[PCl3=N(—PCl2=N)3—PCl3]+SbCl6−,
[PCl3=N(—PCl2=N)3—PCl3]+NbCl6−,
[PCl3=N(—PCl2=N)4—PCl3]+PCl6−,
[PCl3=N(—PCl2=N)4—PCl3]+Cl−,
[PCl3=N(—PCl2=N)5—PCl3]+PCl6−,
[PCl3=N(—PCl2=N)5—PCl3]+BCl4−,
[PCl3=N(—PCl2=N)6—PCl3]+PCl6− and
[PCl3=N(—PCl2=N)6—PCl3]+TaCl6− and
[PCl3=N—PCl(N=PCl3)=N—PCl3 ]+Ci−,
[PCl3=N—PCl(N=PCl3)=N—PCl3]+PCl6−,
[$PCl_3$=N—P(N=PCl3)2=N—PCl3]+Cl− and
[PCl3=N—P(N=PCl3)2=N—PCl3]+HgI3−, where
[PCl3=N—PCl3]+Cl−,   [PCl3=N—PCl3]+PCl6−,
[PCl3=N—PCl2=N—PCl3]+Cl−,
[PCl3=N—PCl2=N—PCl3]+$PCl_6^-$,
[PCl3=N—PCl2=N—PCl3]+SbCl6−,
[PCl3=N(—PCl2=N)2—PCl3]+Cl−,
[PCl3=N(—PCl2=N)2—PCl3]+PCl6−,
[PCl3=N(—PCl2=N)2—PCl3]+SbCl6−,
[PCl3=N(—PCl2=N)3—PCl3]+Cl−,
[PCl3=N(—PCl2=N)3—PCl3]+PCl6−,
[PCl3=N(—PCl2=N)4—PCl3]+Cl−, and
[PCl3=N(—PCl2=N)4—PCl3]+PCl6− and preferably employed and [PCl3=N—PCL3]+PCl6−,
[PCl3=N—PCl2=N—PCl3]+PCl6−,
[PCl3=N(—PCl2=N)2—PCl3]+PCl6− and
[PCL3=N(—PCl2=N)3—PCl3]+PCl6− are more preferably employed.

The preparation of the ionic phosphazenes of formula (V) is known. Reference may be made to M. Bermann: "The Phosphazatrihalides", Advances in Inorganic and Radiochemistry 14 (1972), Academic Press New York, London, pages 1 to 30.

Linear compounds [PCl3=N(—PCl2=N)$_n$—PCl3]+PCl6− can be prepared easily by reaction of phosphorus pentachloride with ammonium chloride or cyclic dichlorophosphazenes, such as (PNCl2)3 or (PNCl2)4. By heating, with release of phosphorus pentachloride, the compounds can be converted into the corresponding chlorides [PCl3=N(—PCl2=N)$_n$—PCl3]+Cl−. These in turn react with halogen compounds of the formula [M$_m$D$_m$], in which M, D and m are the same as above, to give compounds of the formula

[PCl3=N(—PCl2=N)$_n$—PCl3]+[M$_m$D$_{m+1}$]−.

Compounds containing hydroxyl groups which can be used in the process for the preparation of oxygen-containing chlorophosphazenes are both organic and inorganic compounds.

The compounds containing hydroxyl groups are preferably water, alcohols, carboxylic acids, phosphoric and phosphonic acids and monoesters thereof, sulfonic acids, silanols and organopolysiloxanes having Si-bonded hydroxyl groups, where water, alcohols having 1 to 6 carbon atoms, such as methanol, ethanol, isopropanol, 1-butanol, 1-pentanol and cyclohexanol, carboxylic acids, such as formic acid and acetic acid, silanols, such as trimethylsilanol and triphenylsilanol and organopolysiloxanes containing hydroxyl groups, such as pentamethyldisiloxanol, are more preferred.

The molar use ratio of ionic chlorophosphazene of formula (V) and compound containing hydroxyl groups depends on the desired structure of the oxygen-containing chlorophosphazene of formula (VI) and on the nature of the anion A in formula (V). If the anion A is unreactive towards the compound containing hydroxyl groups under the reaction conditions chosen, for example, with compounds having a simple halide as A, an oxygen-containing chlorophosphazene of formula (VI) in which Y is Cl is obtained with 1 mole of a compound containing a hydroxyl group per mole of ionic chlorophosphazene of formula (V). An oxygen-containing chlorophosphazene of formula (VI) where Y is the hydroxyl group is formed with a compound containing two equivalents of hydroxyl groups.

Otherwise, if the anion A is reactive towards the compound containing hydroxyl groups under the reaction conditions chosen, for example, with PCl6− as A, this should be taken into account when choosing the use ratio. An oxygen-containing phosphazene of formula (VI) in which Y is Cl is obtained with 2 mole of a compound containing a hydroxyl group and 1 mole of phosphazene of formula (V) where A is PCl6−, and an oxygen-containing phosphazene of formula (VI) in which Y is a hydroxyl group is obtained with 3 mole of a compound containing a hydroxyl group and 1 mole of phosphazene of formula (V) where A is PCl6−.

Preparation of oxygen-containing chlorophosphazenes of formula (VI) in which Y represents a hydroxyl group can be carried out by the process, starting from ionic chlorophosphazenes of formula (V), not only in one but in two stages.

If the process is carried out in two stages, the hydroxyfunctional compound is initially reacted with the ionic chlorophosphazene only in an amount that the oxygen-containing chlorophosphazene of formula (VI) where Y is chlorine is formed, this then reacts, optionally after isolation, with an equivalent of a compound containing hydroxyl groups to give the phosphazene of formula (VI) where Y is a hydroxyl group. This procedure is preferred if very pure oxygen-containing phosphazenes containing hydroxyl groups are desired and the oxygen-containing chlorophosphazenes of the first stage are easier to clean than the hydroxyfunctional end products because they are solids which crystallize readily or liquids which can be distilled.

The process for the preparation of oxygen-containing phosphazenes can be carried out in the presence or absence of an organic solvent, an organic solvent preferably being employed.

If organic solvents are employed, they are preferably those in which the oxygen-containing phosphazenes dissolve and which are free from hydroxyl groups. The organic solvent employed primarily ensures good distribution of the compounds containing hydroxyl groups, whether these are dissolved or merely dispersed, and allows efficient removal of the heat of reaction, which is of importance for the selectivity of the reactions.

If an organic solvent is employed in the process, it is preferably used in amounts of 50% to 1000% by weight, more preferably 100% to 500% by weight, based on the weight of ionic chlorophosphazene of formula (V).

Examples of organic solvents which can be employed in the process for the preparation of oxygen-containing phosphazenes are essentially those which are liquid under the pressure of the surrounding atmosphere at a temperature of about 0° C. and which have a boiling point under a pressure of about 100 Pa of not more than 150° C., which means they can be removed again by distillation without the products being exposed too severely to heat, and which are largely resistant to hydrogen chloride and phosphorus-chlorine groups, for example, aliphatic and aromatic hydrocarbons, chlorinated hydrocarbons, esters, ethers or acid amides, and mixtures of these solvents.

The organic solvents which can be employed in the process for the preparation of oxygen-containing chlorophosphazenes are preferably aliphatic and aromatic hydrocarbons and chlorohydrocarbons, where n-hexane, cyclohexane, toluene, xylene and chloroform are more preferred.

The process for the preparation of oxygen-containing phosphazenes is preferably carried out at a temperature of 0° C. to 120 ° C., more preferably 20 ° C. to 70 ° C., under a pressure of between 900 and 1100 hPa. However, the process can likewise be carried out under higher or lower pressures.

The individual constituents employed in the process can be one type of constituents or a mixture of constituents.

According to a preferred embodiment of the process, an organic solvent which is free from hydroxyl groups is added to at least one ionic phosphazene of formula (V) and, after the mixture has been adjusted to the desired reaction temperature, at least one hydroxy-functional compound is metered in, optionally as a mixture with an organic solvent, at a rate such that the reaction temperature remains within the given range during the exothermic reaction. The end of the reaction is indicated by the fact that the evolution of hydrogen chloride stops and no further heat effect occurs.

If an organic solvent in which the hydroxy-functional compound is insoluble but the oxygen-containing chlorophosphazene is soluble is employed in the process, the end of the reaction can also be recognized by the disappearance of the compound containing hydroxyl groups.

When the process has ended, the oxygen-containing chlorophosphazenes of the formula (VI) thus obtained can be isolated in a manner known per se, various isolation methods being used, for example, distillation or extraction, depending on the nature of the starting compounds, ionic phosphazene of formula (V) and hydroxy-functional compound employed. Preferably, the oxygen-containing chlorophosphazenes prepared are isolated by all the other constituents of the reaction mixture being removed by distillation, optionally under reduced pressure.

The process has the advantage that oxygen-containing chlorophosphazenes can be prepared in a simple manner. Another advantage is the high selectivity of the reaction, which lead to practically quantitative yields. The selectivity is so high that, by choosing corresponding starting ratios of the starting substances, oxygen-containing chlorophosphazenes of formula (VI) where Y is a chlorine atom or hydroxyl group can be prepared in a completely controlled and reproducible manner. The oxygen(s) is/are thus bonded reproducibly to the same position(s) in the phosphazene molecule, although several phosphorus-chlorine groups are present.

The oxygen-containing chlorophosphazenes containing organosilicon radicals can be employed for all the purposes for which phosphazenes have been employed to date.

The present invention further relates to a process for the condensation and/or equilibration of organosilicon compounds in the presence of oxygen-containing chlorophosphazenes containing organosilicon radicals.

The oxygen-containing chlorophosphazenes containing organosilicon radicals employed in the process are preferably those of formula (I), where compounds of the formula

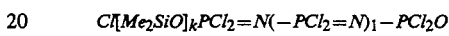

$$Cl[Me_2SiO]_kPCl_2=N(-PCl_2=N)_l-PCl_2O$$

where
k is a number from 2 to 400,
l is a number from 1 to 3 and
Me is the methyl radical, are more preferred.

The amounts of oxygen-containing chlorophosphazenes containing organosilicon radicals can be the same as in processes known to date for the preparation of organosilicon compounds by condensation and/or equilibration.

However, because of the high activity of the oxygen-containing chlorophosphazenes containing organosilicon radicals employed, in general lower amounts than in the processes known to date are completely adequate.

The oxygen-containing chlorophosphazenes containing organosilicon radicals which are active as a catalyst for promoting condensation and/or equilibration reactions of organosilicon compounds are preferably employed in amounts of 0.1 to 1000 ppm by weight (parts by weight per million parts by weight), more preferably 1 to 300 ppm by weight, based on the total weight of the organosilicon compounds to be subjected to condensation and/or equilibration.

The oxygen-containing chlorophosphazenes containing organosilicon radicals are preferably employed as pure substances in the process according to the invention.

However, they can, optionally, be employed as a mixture with substances with which the oxygen-containing chlorophosphazenes containing organosilicon radicals do not react, or at least do not react within a few hours, in a manner such that their accelerating action on the condensation and/or equilibration of the organosilicon compound is noticeably reduced. Examples of these are organic solvents.

Any desired organosilicon compounds which has been subjected to condensation and/or equilibration in the presence of catalysts based on phosphazene can be employed as the organosilicon compound in the process.

Condensation reactions of organosilicon compounds are the reactions of two Si-bonded hydroxyl groups with elimination of water, and furthermore, the reaction of an Si-bonded hydroxyl group with an Si-bonded alkoxy group with elimination of alcohol, or with Si-bonded halogen with elimination of hydrogen halide.

Equilibration reactions are understood as meaning the rearrangements of siloxane bonds of siloxane units.

Condensation and equilibration reactions often proceed simultaneously.

Organosilicon compounds which can be employed in the process are generally known and are often represented by the formulae $$E(SiR^4{}_2O)_e SiR^4{}_2E \qquad (VII)$$

and $$(SiR^4{}_2O)_f \qquad (VII)$$

in which

R$^4$ may be identical or different and represents a hydrogen atom or monovalent, optionally substituted hydrocarbon radicals, E may be identical or different and represents a hydroxyl group, the radical $-OR^5$ where R$^5$ is a monovalent organic radical, $-OSiR^4{}_3$ where R$^4$ is the same as above, or a halogen atom, e is 0 or an integer of at least 1, preferably 2 to 1000, more preferably 2 to 500, and f is an integer having a value from 3 to 12, preferably 4 to 8, more preferably 4.

Although not shown by the formulae, up to 5 mole percent of the diorganosiloxane units can be replaced by other siloxane units, such as R$^4$SiO$_{3/2}$ and/or SiO$_{4/2}$ units, in which R$^4$ is the same as above.

The radical R$^4$ is preferably a hydrogen atom or hydrocarbon radicals having 1 to 18 carbon atoms, where hydrocarbon radicals having 1 to 4 carbon atoms, in particular the methyl radical, are more preferred.

Examples of radical R$^4$ are the examples given above for R and the n-octadecyl radical and anthryl and phenanthryl radical.

Examples of monovalent, substituted hydrocarbon radicals R$^4$ are the substituted hydrocarbon radicals mentioned above for the radical R.

The radical R$^5$ is preferably an alkyl radical having 1 to 4 carbon atoms, more preferably the methyl and the ethyl radical.

The viscosity of the organosilicon compounds of formula (VII) employed in the process is preferably between 0.6 and 10$^6$ mm$^2$/s at a temperature of 25° C., more preferably between 10 and 10$^4$ mm$^2$/s.

Examples of compounds of formula (VII) are α,w-dihydroxydimethylpolysiloxane having a viscosity of 80 mm$^2$/s at 25° C., α,w-dihydroxydimethylpolysiloxane having a viscosity of 20000 mm$^2$/s at 25° C., α,w-dichlorodimethylpolysiloxane having a viscosity of 40 mm$^2$/s at 25° C., α,w-bis(trimethylsiloxy)polymethylhydridosiloxane having a viscosity of 25 mm$^2$/s at 25° C., α,w-bis(trimethylsiloxy)polydimethylsiloxane having a viscosity of 20 mm$^2$/s at 25° C., hexamethyldisiloxane and 1,3-divinyl-1,1,3,3-tetramethyldisiloxane.

Examples of compounds of formula (VIII) are hexamethylcyclotrisiloxane, octamethylcyclotetrasiloxane and decamethylcyclopentasiloxane.

If E in formula (VII) represents $-OSiR^4{}_3$, where R$^4$ is the same as above, the compounds are organosilicon compounds which regulate the chain length.

Furthermore, any desired organosilicon compounds which regulate the chain length and which have been possible to co-use in the processes known to date for condensation and/or equilibration in the presence of a catalyst based on phosphazene can be employed in the process.

Such organosilicon compounds which regulate the chain length are preferably, in addition to the compounds of formula (VII) where E is $-OSiR^4{}_3$ those of the formula $$R^6{}_3SiG \qquad (IX),$$

in which

R$^6$ may be identical or different and is the same as R$^4$ above and

G represents a hydroxyl group, the radical $-OR^5$ where R$^5$ is a monovalent organic radical, or a halogen atom.

Examples of the radical R$^6$ are the examples given for R$^4$ as an organic radical.

G is preferably a hydroxyl group, a chlorine atom, the methoxy radical or the ethoxy radical.

Examples of compounds of formula (IX) are trimethylchlorosilane and trimethylmethoxysilane.

The amount of organosilicon compound which regulates the chain length which is employed depends on the desired height of the molecular weight of the organopolysiloxanes prepared by condensation and/or equilibration and is already known.

The organosilicon compounds employed are commercially available products or can be prepared by processes customary in silicon chemistry.

The individual constituents employed in the process can be one type of such constituents or a mixture of at least two types of such constituents.

The temperatures and pressures used in the process can be the same as those in the processes known to date for condensation and/or equilibration of organosilicon compounds.

The condensation and/or equilibration reactions are preferably carried out at 50° C. to 200° C., more preferably 80° C. to 160° C.

The condensation and/or equilibration reactions can be carried out under a pressure of the surrounding atmosphere, 900 to 1100 hPa. To facilitate removal of the by-products formed during the condensation, for example, water, HCl or alcohol, the condensation and/or equilibration of the organosilicon compounds is preferably carried out under a pressure below 80 kPa. The condensation in particular the equilibration, can also be carried out under higher pressures.

The process can be carried out either batchwise or continuously.

When the desired viscosity has been reached, the viscosity of the organosilicon compound obtained in the process can be kept constant by a procedure in which the catalyst used, or a reaction product which has been formed from this catalyst by reaction with organosilicon compound to be subjected to condensation and/or equilibration and likewise promotes the condensation and/or equilibration of organosilicon compounds, is inhibited or deactivated by addition of inhibitors or deactivators which have been employed to date in connection with phosphazenes, for example, triisononylamine, n-butyllithium, lithium siloxanolate, hexamethyldisilazane and magnesium oxide.

In order to ensure good distribution of the components employed in the process, the mixture of these substances is preferably agitated while the process is carried out.

The organopolysiloxanes prepared, in particular linear organopolysiloxanes, can be used for all purposes where it has been possible to employ the linear organopolysiloxanes produced by condensation and/or equilibration of organosilicon compounds by processes known to date, for example, for care agents and cosmetic recipes, as thread lubricants, for preparation of organopolysiloxane elastomers, in which case the crosslinking can be carried out by condensation, addition of Si-bonded hydrogen with, for example, SiC-bonded vinyl groups or by formation of free radicals, depending on the nature of the terminal units of the linear organopolysiloxanes, and for the preparation of coatings which repel tacky substances.

The process has the advantage that it is easy to carry out and high yields are achieved.

The oxygen-containing chlorophosphazenes containing organosilicon radicals which are employed and promote the condensation and/or equilibration processes display a high activity.

Furthermore, the oxygen-containing chlorophosphazenes containing organosilicon radicals employed have the advantage that they are particularly suitable for use as the pure substance without addition of an organic solvent, simple and exact metering of small amounts used are possible.

In the examples described below, all parts and percentage data relate to the weight, unless stated otherwise. Furthermore, all the viscosity data are based on a temperature of 25° C. Unless stated otherwise, the following examples were carried out under the pressure of the surrounding atmosphere, about 1000 hPa, and at room temperature, about 20° C., or at a temperature which is established when the reactants are brought together at room temperature without additional heating or cooling.

The following products and product mixtures are obtained in accordance with DE 22 29 514 B, cited above, by reaction of phosphorus pentachloride with ammonium chloride in a $PCl_5$: $NH_4Cl$ ratio in the range from 3:1 to 1.5:1:

phosphazene A: $[PCl_3=N-PCl_3]^+[PCl_6]^-$
phosphazene B: $[PCl_3=N-PCl_2=N-PCl_3]^+[PCl_6]^-$
phosphazene C: a mixture of 5% $[PCl_3=N-PCl_2=N-PCl_2=N-PCl_3]^+[PCl_6^-$ and 95% of $[PCl_3=N(-PCl_2=N)_2-PCl_3]^+[PCl_6]^-$
phosphazene D: a mixture of 15% $[PCl_3=N(-PCl_2=N)_2-PCl_3]^+[PCl_6]^-$ and 85% of $[PCl_3=N(-PCl_2=N)_3-PCl_3]^+[PCl_6]^-$
Me represents the methyl radical.

EXAMPLE 1

64.82 g (0.1 mole) of phosphazene B are dispersed in 100 ml of toluene in a flask with a stirrer and gas outlet, with exclusion of moisture. 3.6 g (0.2 mole) of deionized water are slowly metered into this mixture at room temperature, while stirring, such that the temperature of the mixture does not rise above 40° C. due to the exothermic reaction. The reaction has ended when the reaction mixture is homogeneous and no further HCl gas evolves. The volatile constituents are removed at 30° C. under 100 Pa. 38.2 g of an ocher-colored oil remain, from which colorless crystals precipitate after a short time at 0° C. After 2 hours, all the substance has solidified to a slightly yellowish, waxy solid.

Yield: 32.7 g of $PCl_3=N-PCl_2=N-PCl_2O$.
Melting point: 34° C.

20 g (0.052 mole) of the phosphorylchlorophosphazene prepared above are dissolved in 30 ml of toluene, and 0.94 g (0.052 mole) of water is added, while stirring. After 30 minutes, the mixture is concentrated at 50° C. under 100 Pa. An orange-colored liquid remains.

Yield: 18.5 g of $HO-PCl_2=N-PCl_2=N-PCl_2O$.

EXAMPLE 2

75.83 g of phosphazene mixture C are dispersed in 200 ml of n-hexane in a flask with a stirrer, gas outlet and reflux condenser. 9.21 g (0.2 mole) of anhydrous ethanol are added in portions to this mixture at the boiling point of the hexane, while stirring vigorously. The reaction has ended when no further HCl gas evolves. The two-phase reaction mixture is freed from all the volatile costituents at 30° C. under 100 Pa. A clear brown oil remains.

Yield 47.7 g of a mixture of $PCl_3=N-PCl_2=N-PCl_2O$ (5%) and $PCl_3=N(-PCl_2=N)_2-PCl_2P(95\%)$.

EXAMPLE 3

9.0 g (0.5 mole) of deionized water are added to a solution of 126.4 g of phosphazene C in 250 ml of 1,2,3-trichloropropane at 50° C. in a flask with a gas outlet, and the mixture is stirred at this temperature until no further HCl gas evolves. The solvent is then removed, together with other volatile constituents, at 80° C. under 50 Pa. A brown oily liquid remains as the residue.

Yield: 69.4 g of a mixture of $HO-PCl_2=N-PCl_2=N-PCl_2O(5\%)$ and $HO-PCl_2=N(-PCl_2=N)_2-PCl_2O$ (95%).

EXAMPLE 4

3,6 g (0.2 mole) of deionized water are added dropwise to a dispersion of 86.3 g of phosphazene D in 100 ml of toluene at room temperature in a flask with a gas outlet, while stirring. The rate of addition of the water is adjusted such that the temperature of the mixture does not rise about 40° C. as a result of the exothermic reaction. The reaction has ended when no further HCl gas evolves. The volatile constituents are removed at 40° C. under 200 Pa. A yellow-brown liquid remains.

Yield: 57.1 g of a mixture of $PCl_3=N(-PCl_2=N)_2-PCl_2O(15\%)$ and $PCl_3=N(-PCl_2=N)_3-PCl_2O$ (85%),

EXAMPLE 5

A stream of $SO_2$ gas (about 0.5 l/minute) is passed over 100 g (0,188 mole) of crystalline phosphazene A for one hour. After the volatile constituents have been removed at 50° C. under 100 Pa, a pale yellow oil is obtained, which solidifies to a slightly yellowish, waxy solid at room temperature.

Yield: 49.6 g of $PCl_3$32 $N-PCl_2O$. 20 g (74.3 mmol) of the $PCl_3=N-PCl_2O$ described above and 50 g of α,w-bis(trimethylsiloxy)polydimethylsiloxane having a viscosity of 350 $mm^2s^{-1}$ are stirred at 100° C. in a flask with a stirrer and tap for 2 hours, while simultaneously flushing with a stream of $N_2$. The mixture is then cooled to room temperature. The product, a colorless oily liquid of viscosity 10 $mm^2s^{-1}$, has the following average composition: $(ClMe_2SiO_{\frac{1}{2}})$ $(Me_3SiO_{\frac{1}{2}})_{0.07}(Me_2SiO)_8PCl_2=N-PCl_2O$.

EXAMPLE 6

10 g (26 mmol) of $PC_3=N-PCl_2=N-PCl_2O$, the preparation of which is described in Example 1, are stirred for 3 hours at 120° C. with 195 g of α,w-bis(-trimethylsiloxy)polydimethylsiloxane having a viscosity of 200 $mm^2s^{-1}$, with careful exclusion of moisture. A colorless clear oil (viscosity: 195 $mm^2s^{-1}$) which has the following average composition is thereby obtained:

(ClMe₂SiO½) (Me₃SiO½) (Me₂SiO)₉₆PCl₂=N—PCl₂=N—PCl₂O.

EXAMPLE 7

40 g (103.9 mmol) of PCl₃=N—PCl₂=N—PCl₂O, the preparation of which is described in Example 1, are stirred with 120 g (404.6 mmol) of octamethylcyclotetrasiloxane at 130° C. for 3 hours, with careful exclusion of moisture. After 1 hour, the initially nonhomogeneous reaction mixture is completely clear, and the mixture remains clear at the end of the reaction, even after cooling to room temperature. The colorless liquid (viscosity: 12 mm²s⁻¹) has the average composition (ClMe₂SiO½) (Me₂SiO)₁₄.₅PCl₂=N—PCl₂=N—PCl₂O.

EXAMPLE 8

40 g of a mixture of PCl₃=N—PCl₂=N—PCl₂O (5%) and PCl₃=N(—PCl₂=N)₂—PCl₂O(95%), the preparation of which is described in Example 2, are stirred with 120 g (404.6 mmol) of octamethylcyclotetrasiloxane at 130° C. for 3 hours, with careful exclusion of moisture. After 1 hour, the initially nonhomogeneous reaction mixture is completely clear, and the mixture remains clear at the end of the reaction, even after cooling to room temperature. A clear, slightly yellowish liquid having a viscosity of 15 mm²s⁻¹, which has the average composition, is obtained as the product: (ClMe₂SiO½) (Me₂SiO)₁₉PCl₂=N(—PCl₂=N)₁.₉₅—PCl₂O.

EXAMPLE 9

5 g of a mixture of PCl₃=N(—PCl₂=N)₂—PCl₂O (15%) and PCl₃=N(—PCl₂=N)₃—PCl₂O (85%), the preparation of which is described in Example 4, are stirred with 195 g (657.5 mmol) of octamethylcyclotetrasiloxane at 110° C. for 4 hours. A slightly cloudy, colorless oil of viscosity of 1850 mm²s⁻¹ is obtained as the product. It has the average composition: (ClMe₂SiO½) (Me₂SiO)₃₁₄.₃PCl₂=N(—PCl₂=N)₂.₈₅—PCl₂O.

EXAMPLE 10

1425 g of α,w-dihydroxypolydimethylsiloxane having a viscosity of about 80 mm²s⁻ and 75 g of α,w-bis(trimethylsiloxy)polydimethylsiloxane having a viscosity of about 20 mm²s⁻¹ are heated to 150° C. in a flask with a stirrer, and 0.2 g of the catalyst prepared in Example 6, of average composition (ClMe₂SiO½) (Me₃SiO½) (Me₂SiO) ₉₆PCl₂=N—PCl₂=N —PCl₂O, is added, while stirring. After addition of the catalyst, the pressure in the reaction vessel is reduced to about 100 Pa and the reaction mixture is stirred at 150° C. for an additional 10 minutes. The pressure is then increased again to the value of the surrounding air, and 0.6 g of a basic siloxane mixture which has been prepared by reaction of 5 g of n-butyllithium with 250 g of α,w-bis(trimethylsiloxy)polydimethylsiloxane having a viscosity of 350 mm²s⁻¹ is added for deactivation of the catalyst. An α,w-bis(trimethylsiloxy)polydimethylsiloxane having a viscosity of 4000 mm²s⁻¹ is obtained as the product. It is glass-clear, colorless and odorless and does not change its properties even after storage at about 200° C. for several days.

EXAMPLE 11

0.11 g of the catalyst prepared in Example 8 having the average composition (ClMe₂SiO½) (Me₂SiO)₁₉PCl₂=N(—PCl₂=N)₁.₉₅—PCl₂O is added to 960 g of α,w-bis(trimethylsiloxy)polymethylhydridosiloxane having a viscosity of 25 mm²s⁻and 400 g of α,w-bis(trimethylsiloxy)-polydimethylsiloxane having a viscosity of 350 mm²s⁻¹ in a flask with a stirrer at 120° C. and the mixture is stirred at this temperature for 10 minutes. After cooling to room temperature, 2 g of magnesium oxide are stirred into the reaction mixture for deactivation of the catalyst, and the mixture is then filtered. The product is a colorless clear oil having a viscosity of 35 mm²s⁻¹. It has the composition Me₃Si[OSiMe₂]₁₃.₅[OSiMeH]₃₆.₅OSiMe₃.

EXAMPLE 12

1500 kg/h of α,w-dihydroxypolydimethylsiloxane having a viscosity of about 120 mm²s⁻¹ and 120 g/hour of the catalyst prepared according to Example 9 having the average composition (ClMe₂SiO½) (Me₃SiO₃₁₄.₃PCl₂=N(—PCl₂=N)₂.₈₅—PCl₂ O are metered continuously into a screw reactor. The temperature in the reactor is 160° C. and the pressure is 6 kPa. After an average residence time of about 2 minutes the catalyst is deactivated by continuous addition of 15 ml/hour of triisononylamine. The product, an α,w-dihydroxypolydimethylsiloxane having a viscosity of about 350000 mm²s⁻¹, is colorless, clear and odorless.

What is claimed is:

1. Oxygen-containing chlorophosphazenes containing organosilicon radicals of the formula $$Z-PCl_2=N(-PCl_2=N)_n-PCl_2O \qquad (I)$$

in which

Z is an organosilicon radical bonded to phosphorus via oxygen and n is 0 or an integer from 1 to 6.

2. Oxygen-containing chlorophosphazenes containing organosilicon radicals as claimed in claim 1, in which n is an integer from 1 to 3.

3. Oxygen-containing chlorophosphazenes containing organosilicon radicals as claimed in claim 1, in which Z is an organosilicon radical, bonded to phosphorus via oxygen, consisting essentially of units of the formula $$R_aX_bSiO_{\frac{4-a-b}{2}} \qquad (II)$$

in which

R may be identical or different and represents a hydrogen atom or a monovalent organic radical, X may be identical or different and represents a chlorine atom or a radical —OR¹, where R¹ is a monovalent organic radical, a is 0, 1, 2 or 3, and b is 0, 1 or 2, with the proviso that the sum of a+b is less than or equal to 3.

4. A process for the preparation of an oxygen-containing chlorophosphazene containing organosilicon radicals and having the formula (I)

$$Z-PCl_2=N(-PCl_2=N)_n-PCl_2O \qquad (I)$$

in which

Z is an organosilicon radical bonded to phosphorus via oxygen and n is 0 or an integer from 1 to 6, which consists esentially of reacting at least one oxygen-containing chlorophosphazene of the formula $PCl_3=N(-PCl_2=N)_n-PCl_2O$ (III), in which n is o of an integer from 1 to 6, with at least one organosilicon compound consisting essentially of units of the formula

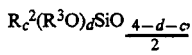 (IV)

in which

R² may be identical or different and is the same as the radical R,

R³ may be identical or different and is the same as the radical R¹ above, c is 0, 1, 2 or 3, and d is 0, 1, 2 or 3, with the proviso that the sum of c+d is less than or equal to 4.

5. The process as claimed in claim 4, wherein the organosilicon compound consisting essentially of units of formula (IV) is employed in amounts of 20% to 1000% by weight, based on the total weight of the oxygen-containing chlorophosphazenes of formula (III).